(12) United States Patent
Ushiyama

(10) Patent No.: US 6,331,429 B1
(45) Date of Patent: Dec. 18, 2001

(54) CULTURE MEDIUM FOR MICROORGANISMS

(75) Inventor: Masashi Ushiyama, Yokohama (JP)

(73) Assignee: Chisso Corporation, Osaka-Fu (JP)

( * ) Notice: Subject to any disclaimer, the term of this patent is extended or adjusted under 35 U.S.C. 154(b) by 0 days.

(21) Appl. No.: 09/225,467

(22) Filed: Jan. 6, 1999

Related U.S. Application Data

(63) Continuation of application No. PCT/JP97/02470, filed on Jul. 16, 1997.

(30) Foreign Application Priority Data

Jul. 17, 1996 (JP) ........................................ 8-207914

(51) Int. Cl.⁷ .............................. C12N 1/00; C12N 1/20; C12Q 1/00; C12Q 1/02; C12Q 1/24
(52) U.S. Cl. .................... 435/243; 435/4; 435/29; 435/30; 435/252.1; 435/253.6
(58) Field of Search ................ 435/243, 252.1, 435/253.6, 4, 29, 30

(56) References Cited

U.S. PATENT DOCUMENTS

| | | | |
|---|---|---|---|
| 3,814,670 | 6/1974 | Freake et al. | 195/127 |
| 3,843,452 | 10/1974 | Freake et al. | 195/103.5 |
| 3,881,993 | 5/1975 | Freake et al. | 195/139 |
| 4,250,256 | 2/1981 | Wielinger et al. | 435/32 |
| 4,411,795 | * 10/1983 | Olson | 210/679 |
| 4,565,783 | 1/1986 | Hansen et al. | 435/299 |

FOREIGN PATENT DOCUMENTS

| | | |
|---|---|---|
| 54-132292 | 10/1979 | (JP) . |
| 3-15379 | 1/1991 | (JP) . |
| 4-117299 | 4/1992 | (JP) . |
| 5-505522 | 8/1993 | (JP) . |
| 7-501943 | 3/1995 | (JP) . |
| 7-289285 | 11/1995 | (JP) . |
| WO 82/02563 | 8/1982 | (WO) . |

* cited by examiner

*Primary Examiner*—Michael G. Wityshyn
*Assistant Examiner*—Deborah K Ware
(74) *Attorney, Agent, or Firm*—McDermott, Will & Emery

(57) ABSTRACT

A material for culture media comprises a fiber layer; a polymeric compound layer A free of a color former and a selecting agent; and a polymeric compound layer B containing a color former and/or a selecting agent, which are put in layers in this order. The material permits the precise and rapid microbial test of subjects having a curvature or unevenness to some extent. In addition, the material can save space required for the test and can reduce the amount of waste generated after the practical use thereof.

12 Claims, 2 Drawing Sheets

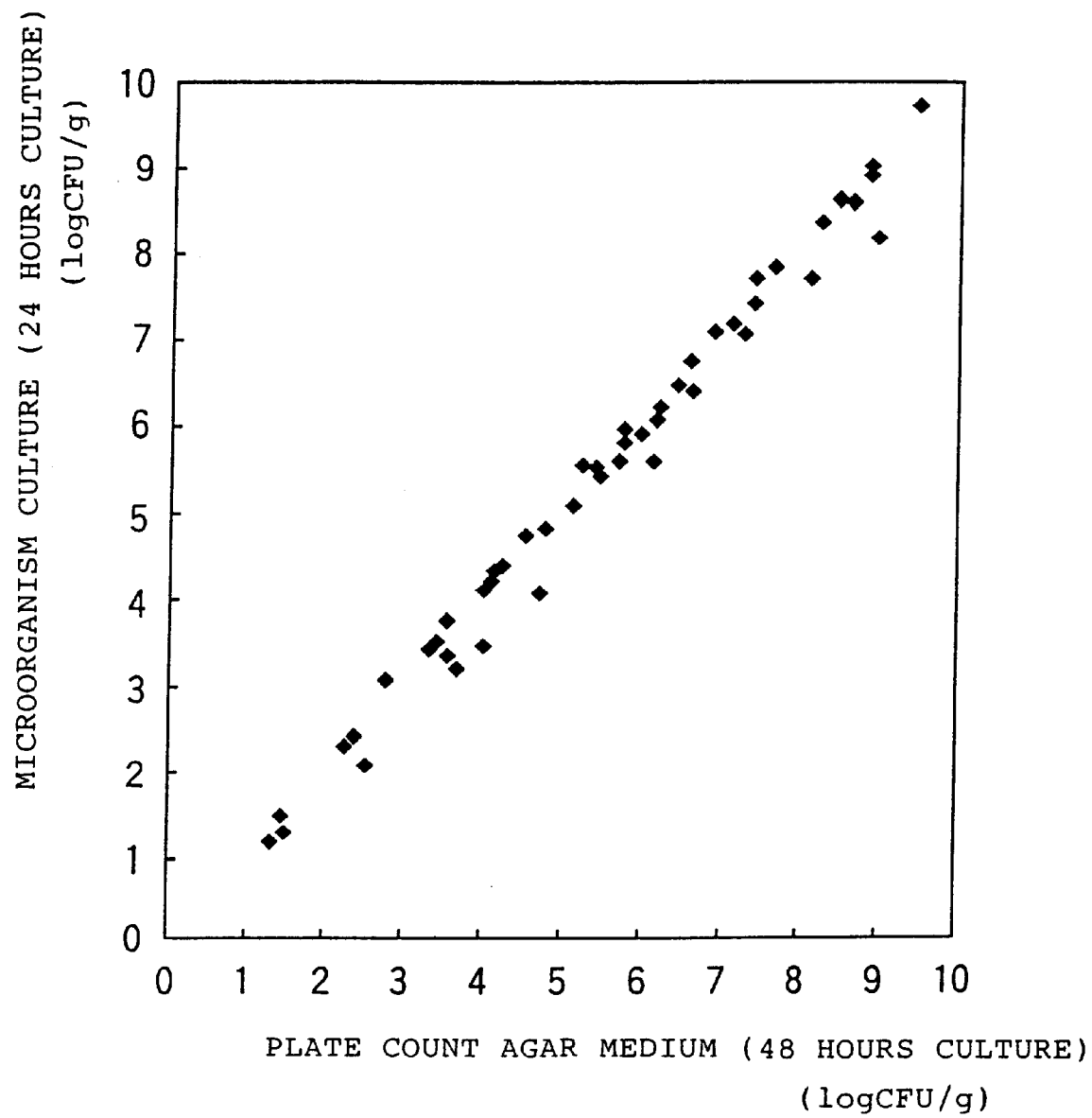

CULTURE MEDIUM FOR MICROORGANISMS

REFERENCE TO RELATED APPLICATION

This Application is a continuation of International Application No. PCT/JP97/02470, whose international filing date is Jul. 16, 1997, which in turn claims the benefit of Japanese Patent Application No. 8/207914, filed Jul. 17, 1996, the disclosures of which Applications are incorporated by reference herein. The benefit of the filing and priority dates of the International and Japanese Applications is respectfully requested.

TECHNICAL FIELD

The present invention relates to a material for culture media and a culture medium. More specifically, the present invention relates to a material for culture media and a culture medium for culture and detection of microorganisms present in foods and environment.

PRIOR ART

The conventional method for culturing and detecting microorganisms will be described below, while taking the determination of standard plate count in the food test by way of example. First, a dehydrated agar culture medium is dissolved and sterilized and then stored at a temperature of about 45° C. A predetermined amount of the agar medium is dispensed in a sterilized Petri dish to which a predetermined amount of a sample to be examined such as a food suspension has previously been added, followed by pour culture, solidification of the agar, culture at a predetermined temperature and then determination of the number of colonies formed. As has been described above, the conventional method for culturing microorganisms requires much labor and time since it requires the preliminary preparation of a culture medium and the sterilization thereof and the agar media should be maintained at a temperature at which it is not solidified. To carry out the microbial test rapidly and more simply, it is desirable that such preparation of a culture medium, which requires much labor and time, can be eliminated. In addition, the conventional method also suffers from a problem in that a large number of plastic Petri dishes must generally be used for the preparation of the medium and this in turn results in the generation of a large quantity of plastic waste after the culture of microorganisms.

The environmental microbial test has in general been carried out by wiping a subject to be examined with a swab, rinsing the swab with sterilized water or sterilized physiological saline to thus form a suspension of the bacterial cell bodies adhered to the swab, smearing the suspension onto an agar medium previously prepared or culturing them through pour culture by the same method described above and finally determining the number of colonies formed thereon.

On the other hand, there has been put on the market a simplified culture medium capable of eliminating the labor required for the preparation thereof. The simplified culture may be classified, for convenience, into stamp-type (Japanese Un-Examined Patent Publication (hereinafter referred to as "J. P. KOKAI") No. Hei 4-117299), filter-type, film-type (Japanese Examined Patent Publication (hereinafter referred to as "J. P. KOKOKU") No. Hei 2-49705; and J. P. KOKAI No. Hei 3-15379) and test paper-type ones. The stamp-type simplified medium is one in which an agar medium is dispensed in a plastic container to above the rim and the surface of which can be brought into direct contact with a subject upon test. The simplified medium of this type is easily used and is favorable for simple environmental test for microbial contamination, but the medium is insufficient in the ability of quantitative analysis because of a small area thereof Therefore, it is difficult to examine subjects having curvatures or uneven surfaces and the culture medium of this type cannot be used in the usual food test and environmental test. Moreover, the medium requires the use of a plastic container and this accordingly leads to the generation of a large quantity of plastic waste after the culture like the aforementioned conventional methods. The filter-type simplified culture medium is favorable for the test of liquid samples, but is unfavorable for the test of samples other than liquid ones. In the test paper-type one, colonies are formed within the test paper or the like and therefore, the media suffers from a problem in that the colonies formed are not easily observed and the medium does not ensure good quantitative properties. The film-type simplified culture medium permits quantitative test of foods and can easily be used, but the medium of this type cannot be brought into direct contact with a subject to be tested, unlike the stamp-type one, when examining, for instance, environments. In addition, the number of bacterial cells or colonies cannot always be determined because of the presence of bacterial cells capable of dissolving gels.

There have been put on the market several types of simplified culture media that are designed in such a manner that they can easily be used depending on various purposes. However, there has not yet been developed any simplified culture medium that can, in itself, be used in various applications such as the food test and direct test of subjects.

On the other hand, a color-developing agent such as a tetrazolium salt and/or a color former such as a fluorescent substrate (hereunder simply referred to as "color former") are sometimes added to a culture medium so that the growth of microorganisms can easily be confirmed. However, these color formers may sometimes inhibit the growth of microorganisms and there has often been observed a low correlation between the results obtained in the presence or absence of these color formers depending on the kinds of sample microbial florae. Moreover, a selecting agent is often added to a culture medium to control the growth of the microorganisms other than those which should be detected, but it is common that the selecting agent also serves to inhibit the growth of the latter and to thus often retard the growth thereof.

SUMMARY OF THE INVENTION

Accordingly, it is an object of the present invention to provide material for culture media and a culture medium which permit easy test of bacterial cells present in a variety of subjects to be tested. More specifically, an object of the present invention is to provide material for culture media and a culture medium which permit quantitative test of microorganisms present in foods or environments by wiping, with a swab or the like, a food suspension or a subject to be tested in an environment, dispersing the bacterial cells adhered to the swab in water to give a suspension and then adding the suspension to a culture medium prepared from the material. These material for culture media and culture medium also permit the direct contact test wherein they are brought into contact with a subject to be tested, directly if the subject is in a wet condition or after wetting them through addition of sterilized water if it is in a dry state. Moreover, these material for culture media and culture medium also permit the inhibition of any direct contact between the microorganisms and a color former and/or a selecting agent at the initial stage of the culture and in turn permit the reduction of the influence of these agents on the growth of the microorganisms to be tested.

According to the present invention, there are provided the following material for culture media and culture media:

(1) Material for culture media comprising a fiber layer, a layer A of a polymeric compound free of a color former and a selecting agent and a layer B of a polymeric compound containing a color former and/or a selecting agent, which are laminated together in this order.

(2) The material for culture media according to the foregoing item (1) wherein a polymeric compound whose 4% by weight aqueous solution has a viscosity, as determined at 20° C., of 10 cps is used as the polymeric compound for forming the layers A and B.

(3) A medium for culturing microorganisms comprising nutrients required for the growth of microorganisms, which are incorporated into at least one of the layer A, the layer B and the fiber layer of the material for culture media according to the foregoing item (1) or (2).

The culture medium of the present invention is one prepared by incorporating nutrients into the material for culture media according to the present invention. The material for culture media and the culture medium of the present invention are a dry material for culture media and a dry culture medium which can be converted into a culture medium to which water or nutrient-containing water is added to give a culture medium capable of growing microorganisms. They are also characterized in that the contact between microorganisms and a color former and/or a selecting agent is inhibited at the initial stage of the culture.

BRIEF DESCRIPTION OF THE DRAWINGS

FIG. 2 is a graph showing the correlation between the total viable counts observed when culturing microorganisms on the culture medium prepared in Comparative Example 1 and the conventional plate count agar medium.

BEST MODE FOR CARRYING OUT THE INVENTION

Figure 1:
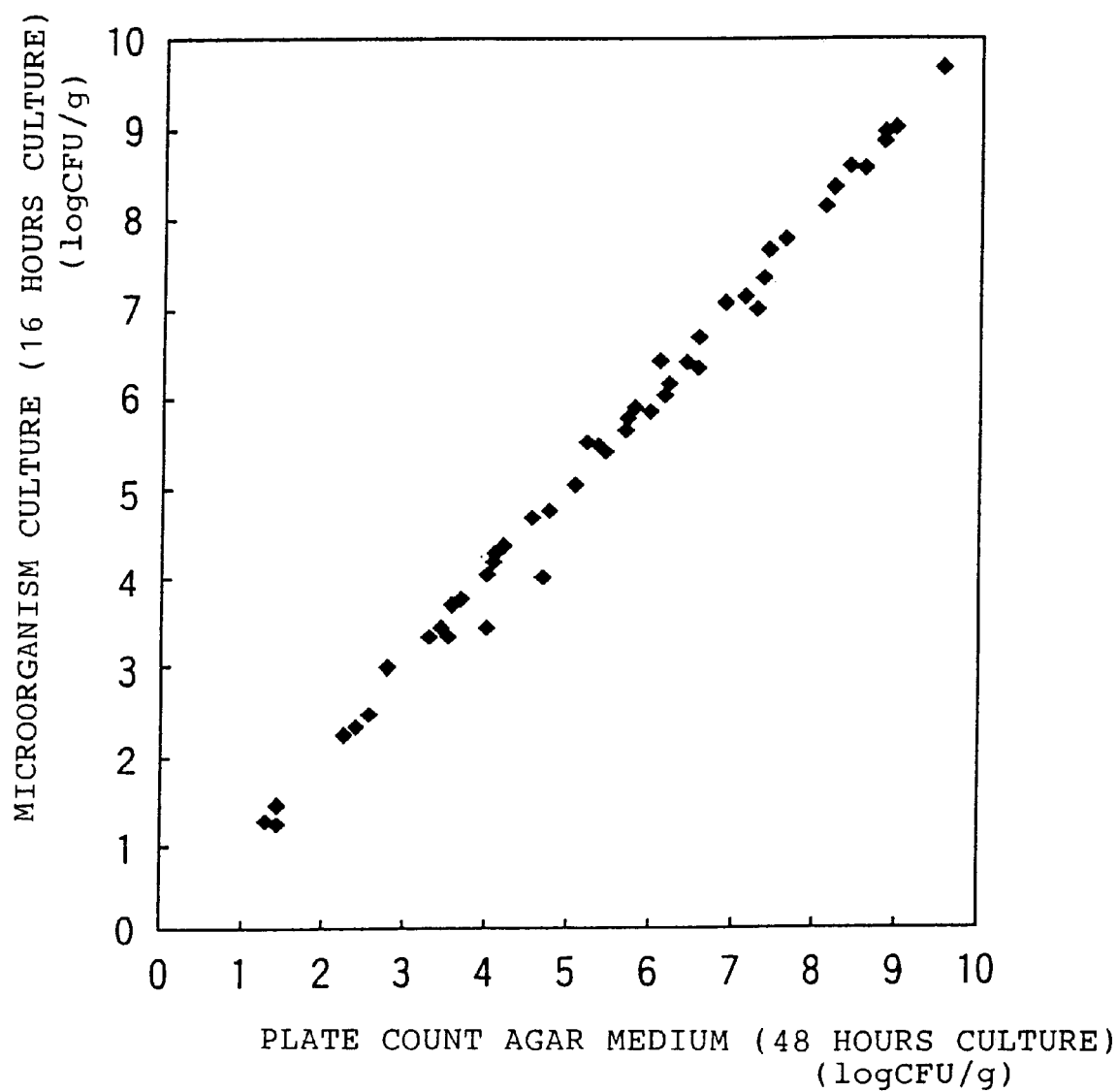
FIG. 1 is a graph showing the correlation between the total viable counts observed when culturing microorganisms on the culture medium prepared in Example 1 and the conventional plate count agar medium.

The method for preparing a material for culture media or a culture medium according to the present invention will be described in detail below.

First, a film (a layer B of a polymeric compound) is formed by applying an aqueous solution of a polymeric compound containing a color former and/or a selecting agent or an aqueous solution of a polymeric compound containing a color former and/or a selecting agent and nutrients onto a film-like substrate of, for instance, a polyester and then drying the same. Next, a layer A of a polymeric compound is formed on the film (the layer B of a polymeric compound) by applying an aqueous solution of a polymeric compound or a nutrient-containing aqueous solution of a polymeric compound (free of any color former and/or any selecting agent) onto the film. A fiber layer is then formed thereon by loading fibers or nutrient-impregnated fibers onto the layer A without drying or after semi-drying or completely drying the layer A; and thereafter drying the fibers. The resulting assembly is, if necessary, dried, followed by cutting it into pieces having a desired size with or without removal of the film-like substrate of polyester or the like and sterilization of the pieces by, for instance, the ethylene oxide gas sterilization after, if necessary, adhering the pieces to an appropriate support sheet or introducing them into a container such as a bag or a Petri dish to thus give a material for culture medium or a culture medium. In these materials, the two polymeric compound layers A and B and the fiber layer are preferably closely adhered to each other, irrespective of the methods for preparing them.

The material for culture medium and the culture medium of the present invention will be used as follows.

A suspension is first prepared by adding water to a food and then homogenizing it or swabbing, with a swab or gauze, the surface of a subject to be tested such as food-production environments, dispersing the microbial cells adhered to the swab or gauze in water, followed by appropriate dilution of the suspension, addition of the diluted suspension to a culture medium, coverage of the medium with, for instance, a plastic film to thus prevent any evaporation of moisture and subsequent culture of the microorganisms to thus grow them. If using a nutrient-containing water as the diluent, the material for culture medium may be substituted for the culture medium.

When testing a subject through the direct contact test, the material for culture media or the microorganism culture medium of the present invention is wetted by addition of sterilized water or nutrient-containing water, followed by directly stamping the subject with the culture medium or the material, or swabbing the surface of the subject to be tested with the culture medium, coverage of the medium with, for instance, a plastic film as a means for preventing any moisture evaporation, with or without addition of water or nutrient-containing water thereto, and culture of the microorganisms to grow the same.

On the other hand, when testing a wet plane, the plane is swabbed with the material for culture media or the microorganism culture medium without preliminary moistening of the medium, or the subject is directly stamped with the culture medium or the material, followed by coverage of the medium with, for instance, a plastic film as a means for preventing any moisture evaporation, with or without addition of water or nutrient-containing water thereto, and culture of the microorganisms to grow the same.

As has been described above, the material for culture media or the culture medium of the present invention permits the test of microorganisms present on the surface of the usual foods or subjects to be tested in various environments according to the usual methods. In addition, the material or the culture medium also permits the test of subjects to be tested by the direct contact test or by a method that comprises the step of directly swabbing the surface of the subject with the material or the medium. In addition, when testing a subject by the direct contact test or the direct swabbing method, the subject to be tested may have a curvature or unevenness to some extent.

When a sample liquid is added to the material or the culture medium from its fiber layer side, the liquid is once held in the fiber layer. The polymeric compound present in the layer A adjacent to the fiber layer is gradually dissolved with water held in the fiber layer and the resulting polymer solution becomes viscous to thus prevent any migration of the microorganisms and simultaneously, the microorganisms grow and initiate division. Thereafter, the water also dissolve the polymer present in the underlying layer B, and if the layer B contains a color former, the microorganisms come in contact with the color former and the latter develops a color which permits the confirmation of the growth condition of the microorganisms. Moreover, if the layer B contains a selecting agent, the microorganisms come in contact with the selecting agent to inhibit any growth of the microorganisms other than those interested, but the latter continues to grow.

The microorganisms present in a sample liquid are distributed throughout the entire fiber layer when the sample liquid is added to the material or the culture medium. However, the polymeric compound on the surface of the layer A is gradually dissolved the water present in the fiber layer and for this reason, the microorganisms cannot penetrate into the layer A. More specifically, the microorganisms are forced up to the surface of the fiber layer during the processes of the gradual dissolution of the polymer in the layer A and of incorporation of the fiber layer and the dissolved polymer. Thus, the microorganisms form colonies only on the surface of the fiber layer. Thus, the colonies are formed only on the surface of the fiber layer and thus the number of the colonies formed can precisely be determined unlike the culture medium using filter paper wherein the colonies are formed within the filter paper.

Fibrous materials for constituting the fiber layer may be, for instance, nylon fibers, acrylic fibers, cellulose fibers, pulp fibers, rayon fibers, polyester fibers, polyolefin fibers, wool, silk, cotton, glass fibers, polyurethane fibers, or the foregoing fibers modified by, for instance, hydrophilization treatments, or composites thereof. These fibers are processed into, for instance, sheet-like materials such as nonwoven fabrics or textile fabrics and then used as the fiber layer. The fibers must not always be hydrophilic, but the use of hydrophilic fibers or hydrophilized fibers would ensure a high water-absorption rate, the improvement of working efficiency and good dispersibility of the colonies formed as a result of the growth of the microorganisms. Nylon fibers are particularly preferred. When nylon fibers are used, there is not observed any deviation of the colony distribution even when a small amount of a sample liquid is added to the culture medium, or water is additionally added to the medium after stamping or swabbing the surface of a subject with the medium. In other words, the colonies are uniformly distributed on the whole surface of the fiber layer. The average diameter of the fibers used in the fiber layer is preferably as small as possible, but in general ranges from 1 to 30 $\mu$m and more preferably 1 to 6 $\mu$m. The thickness of the fiber layer is suitably (0.04 to 3) ×20×a/b mm, if the amount of the sample liquid is assumed to be a ml and the area of the medium is assumed to be b cm². For instance, if 1 ml of a sample liquid is added to the medium having an area of 20 cm², the thickness of the fiber layer preferably ranges from 0.04 to 3 mm and the basis weight thereof preferably ranges from 50 to 200 g/m².

The layers A and B are preferably in a film-like or sheet-like form. Polymeric compounds used for preparing these layers A and B are preferably those whose 4% by weight aqueous solution has a viscosity of not less than 10 cps and preferably 15 to 120 cps, as determined at 20° C. using a B-type viscometer and which never inhibit the growth of microorganisms. Examples of such polymeric compounds usable herein include polyvinyl alcohol, cellulose derivatives, polyacrylic acid derivatives, starch derivatives, proteins, protein derivatives and polysaccharides, with polyvinyl alcohol being more preferred. Particularly preferred are polyvinyl alcohols having a degree of saponification ranging from 75 to 90% and a molecular weight ranging from 30,000 to 200,000. The term "polyvinyl alcohol" herein used includes modified polyvinyl alcohols and cross-linked products of polyvinyl alcohols or modified polyvinyl alcohols.

The thickness (dry state) of the layer A is suitably (5 to 80) ×20×a/b (g/cm²) as expressed in terms of the amount of the polymeric compound and that (dry state) of the layer B is suitably (10 to 150) ×20×a/b (g/cm²). Moreover, the total thickness of the layers A and B (dry state) is desirably (40 to 200) ×20×a/b (g/cm²). The polymeric compounds used in these layers A and B may be the same or different.

It is advantageous to preliminarily add a color former, for instance, a tetrazolium salt such as 2,3,5-triphenyl tetrazolium chloride or a pH indicator to the material or the culture medium. This is because the growth of microorganisms can easily be recognized since the color former develops or changes a color as the microorganisms grow. However, these color formers adversely affect the growth of microorganisms and in some cases, the color former may inhibit the growth of microorganisms, depending on the kinds and/or conditions thereof. It has been known that 2,3,5-triphenyl tetrazolium chloride that is frequently used for confirming the growth condition of microorganisms has an effect of inhibiting the growth of gram-positive bacteria such as staphylococci. The addition of a color former to the medium makes the observation of the colonies formed easy, but the growth of a part of microorganisms is inhibited. Therefore, the number of microbial cells would sometimes be reduced as compared with that observed when cultured in a medium free of any color former depending on the microbial flora.

Moreover, a selecting agent is often added to a culture medium in order to control the growth of microorganisms other than those interested in the test. An agent having a strong effect of inhibiting the growth of microorganisms is frequently used as the selecting agent and accordingly, the agent shows an inhibitory effect on not only the growth of microorganisms other than those interested, but also the growth of the target microorganisms. Thus, the selecting agent often retards the growth of the target microorganisms. This retardation of the growth of the target microorganisms becomes a cause of an extension of the time required for test.

The use of the material for culture media and the culture medium of the present invention permits the inhibition of any direct contact between the microorganisms and the color former and/or the selecting agent during the initial growth stage of the microorganism. This is because, the material or the culture medium is prepared by putting a polymer layer A free of a color former and/or a selecting agent on a polymer layer B containing a color former and/or selecting agent, then putting a fiber layer on the layer A and a sample liquid is applied onto the culture medium from the fiber layer side.

For this reason, the use of the culture medium of the present invention permits the relief of the growth inhibitory effect of the color former on microorganisms and thus the viable cell count is not significantly reduced as compared with the culture medium free of any color former. In addition, the time required for culture can be reduced. For instance, the time required for carrying out a test which usually requires two days for culture can be reduced to one day, if the direct contact between the microorganisms and the selecting agent during the initial growth stage of the microorganism is inhibited.

Examples of the color formers used in the present invention are tetrazolium salts such as 2,3,5-triphenyl tetrazolium chloride, tetrazolium violet and 2-(4-iodophenyl)-3-(4-nitrophenyl)-5-phenyl-2H tetrazolium chloride; pH indicators such as Bromothymol Blue, Bromophenol Purple, Phenol Red and Thymol Blue; Brilliant Black; and color-developing substrates for enzyme. The amount of the color former used may vary depending on the kind of the color former used, but preferably ranges from 0.05 to 1000 $\mu g/cm^2$ based on the unit area of the material for culture media or the culture medium.

In addition, the selecting agents usable herein may be those currently used in this field. By way of example, specific examples thereof include Brilliant Green for the separation of salmonella; common salt, glycine, lithium chloride and tellurites for the separation of Staphylococcus aureus strains. The amount of the selecting agent may vary depending on the kind thereof, but is preferably approximately identical to that currently used in the agar culture medium, i.e., 0.01 to 5000 $\mu g/cm^2$ on the basis of the unit area of the material for culture media or the culture medium.

The nutrients incorporated into the culture medium for microorganisms are not restricted to any specific one inasmuch as they are favorable for the microorganisms to be cultured. For instance, there may be used in the invention ingredients for culture media, such as those obtained by removing the agar from the commonly used liquid media and agar media. The selecting agent which is an agent for controlling the growth of any microorganism other than the target ones to be detected and/or a dye for making colonies formed easily visible or the color former or a color-developing or fluorescent substrate for enzyme for detecting specific microorganisms are incorporated into only the polymer layer B which does not come in close contact with the fiber layer.

Examples of nutrients usable in the invention include yeast extract-peptone-dextrose mixtures, meat extract-peptone mixtures, peptone-soybean peptone-dextrose mixtures and these mixtures to which potassium monohydrogen phosphate and/or sodium chloride are added for the test of the indicator organisms; peptone-ammonium iron citrate-sodium chloride-potassium monohydrogen phosphate-lactose mixtures and peptone-lactose-potassium monohydrogen phosphate mixtures for the test of E. coli and coliform; meat extract-peptone-sodium chlolide-mannit-yolk mixtures and peptone-meat extract-yeast extract-sodium pyrubate mixtures for the test of Staphylococci; yeast extract-peptone-sucrose-sodium citrate-ferric citrate-sodium chloride mixtures for the test of Vibrios; bovine brain extract-heart extract-peptone-glucose-potassium momohydrogen phosphate-sodium nitride mixtures for the test of Enterococci; and peptone-grape sugar mixture and potato extract-grape sugar mixtures for the test of yeasts and moulds.

The material for culture media may be reinforced by, for instance, adhering, adsorbing or attaching a solid material as the reinforcing material thereto. Alternatively, the culture medium for microorganisms may likewise be reinforced by, for instance, adhering, adsorbing or attaching a solid material as a reinforcing layer to the culture medium. The reinforcing material is preferably those having a small thickness such as a film or sheet while taking into consideration space saving.

Moreover, the material for culture media or the culture medium may be reinforced by mixing at least one member thereof with a reinforcing material and then forming the resulting mixture into a desired shape to thus give a reinforced culture medium.

In addition, a cover of, for instance, a plastic film may be applied to the material for culture media or the culture medium.

EXAMPLES

The present invention will hereinafter be described in more detail with reference to the following working Examples, but the present invention is not restricted to these specific Examples at all.

Example 1

To one liter of water, there were added 50 g of a polyvinyl alcohol having a degree of saponification of 88% and an average degree of polymerization of 1800, 2 g of meat extract, 6 g of peptone, 2 g of sodium chloride, 2 g of potassium monohydrogen phosphate and 10 mg of 2,3,5-triphenyl tetrazolium chloride, followed by dissolution thereof with heating, applying the resulting mixture onto a 1×1 m polyester film having a thickness of 20 $\mu$m and drying the coated layer to form a polymer layer B comprising the polyvinyl alcohol film. Separately, there were dissolved, in 500 ml of water, 20 g of a polyvinyl alcohol, 0.8 g of meat extract, 2.4 g of peptone, 0.8 g of sodium chloride and 0.8 g of potassium monohydrogen phosphate to form a solution, followed by application of the solution onto the foregoing film and then drying the coated layer to form a polymer layer A comprising the polyvinyl alcohol. A nylon melt-blown nonwoven fabric having a basis weight of 80 g/m$^2$, an average fiber diameter of 2.5 $\mu$m and a thickness of 1 mm was immersed in a 3% by weight aqueous peptone solution, followed by squeezing the fabric, adhering it to the foregoing polyvinyl alcohol film and then drying the resulting assembly to give a culture medium of the present invention. The culture medium was cut into circular pieces each having a diameter of 50 mm to give culture media for growing microorganisms. After adhering a polyester film having a thickness of 100 $\mu$m and a size of 70×80 mm to the culture medium from its polyester film side, the culture medium was sterilized by the ethylene oxide gas sterilization.

To a sterilized bag, there was introduced 10 g each of various foods such as meat, cut vegetable or household dishes, followed by addition of 100 ml of water, homogenization with a stomacher to give a solution, preparation of a series of 10-fold diluted solutions using sterilized water, application of 1 ml each of the dilution solutions to culture media, coverage of the culture media with sterilized polypropylene films having a thickness of 0.04 mm and then culture of microorganisms at 35° C. for 16 hours.

The same diluted solution (1 ml) was added to a sterilized Petri dish, followed by pour culture through addition of solution to a plate count agar medium which had been maintained at 45° C. after sterilization and then culture of microorganisms at 35° C. for 16 hours.

The total viable counts on the culture medium of the present invention and the plate count agar medium were determined and compared with each other. These results obtained showed good correlation between them, as shown in FIG. 1, wherein the correlation coefficient was found to be 0.998.

Comparative Example 1

To one liter of water, there were added 60 g of a polyvinyl alcohol having a degree of saponification of 88% and an average degree of polymerization of 1800, 2.4 g of meat extract, 7.2 g of peptone, 2.4 g of sodium chloride, 2.4 g of potassium monohydrogen phosphate and 10 mg of 2,3,5-triphenyl tetrazolium chloride, followed by dissolution thereof with heating, application of the resulting mixture onto a 1×1 m polyester film having a thickness of 20 $\mu$m and drying of the coated layer to form a polymer layer A comprising the polyvinyl alcohol film. Nylon melt-blown nonwoven fabric having a basis weight of 60 g/m², an average fiber diameter of 2.5 μm and a thickness of 1 mm was immersed in a 3% by weight aqueous peptone solution, followed by squeezing the fabric, adhering it to the foregoing polyvinyl alcohol film A and then drying the resulting assembly to give a comparative culture medium. The culture medium was cut into circular pieces each having a diameter of 50 mm to give culture media for growing microorganisms. After adhering a polyester film having a thickness of 100 μm and a size of 70×80 mm to the culture medium from the polyester film side of the culture medium, the latter was sterilized by the ethylene oxide gas sterilization.

To the resulting culture medium, there was added 1 ml each of the diluted sample liquid prepared in Example 1, followed by coverage thereof with a sterilized polypropylene film having a thickness of 0.04 mm, culture of microorganisms at 35° C. for 24 hours and determination of the total viable counts on the medium to thus compare it with that observed for the plate count agar medium used in Example 1. The results show good correlation with a correlation coefficient of 0.993, but it was observed for a part of samples that the viable counts were reduced to a level of ⅕ to ¹/₁₀ time that determined using the plate count agar medium, as shown in FIG. 2.

Example 2

To one liter of water, there were added 20 g of carboxymethyl cellulose, 30 g of a polyvinyl alcohol having a degree of saponification of 79% and an average degree of polymerization of 2200, 4 g of peptone, 2 g of yeast extract, 2 g of potassium monohydrogen phosphate, 4 g of mannit, 2.4 g of lithium chloride, 4.8 g of glycine, 36 g of sodium chloride, 0.012 g of Phenol Red and 0.0096 g of potassium telluiite, followed by dissolution of these components, application of the resulting solution onto a polyester film having a thickness of 20 μm and a size of 1×1 m and then drying to form a polymeric compound layer B. Then there was applied, onto the layer B, a solution prepared by dissolving, in 500 ml of water, 10 g of a polyvinyl alcohol having a degree of saponification of 88% and an average degree of polymerization of 1800, 0.8 g of peptone, 0.4 g of yeast extract, 0.4 g of potassium monohydrogen phosphate and 0.8 g of mannit, followed by drying the coated solution to form a polymeric compound layer A. A rayon-polyester mixed nonwoven fabric having a basis weight of 80 g/m², an average fiber diameter of 4 μm and a thickness of 1.2 mm was immersed in a 3% by weight aqueous peptone solution, followed by squeezing the fabric, adhering it to the foregoing layer A and then drying the resulting assembly. The assembly was cut into circular pieces each having a diameter of 50 mm. After adhering a polyester film having a thickness of 100 μm and a size of 70×80 mm to the assembly from the polyester film side thereof, the latter was sterilized by the ethylene oxide gas sterilization.

To a sterilized bag, there was introduced 25 g of chicken meat, followed by addition of 225 ml of water, homogenization with a stomacher to give a solution, preparation of a series of 10-fold diluted solutions using sterilized water, application of 1 ml each of the diluted solutions to culture media for microorganisms, coverage of the culture media with sterilized polypropylene films having a thickness of 0.04 mm and then culture of microorganisms at 35° C. for 24 hours. Black colonies were formed on about 15% of the samples. All of the black colonies formed were found to be *Staphylococcus aureus*.

Example 3

The wet face of a chopping board washed with water was directly stamped with a culture medium for microorganisms prepared according to the procedures used in Example 1 from its fiber layer side or directly wiped out with the culture medium. Thereafter, 0.5 to 0.7 ml of sterilized water was added to the medium, followed by coverage with a sterilized polypropylene film having a thickness of 0.04 mm and culture of microorganisms at 35° C. for 24 hours.

In addition, to a culture medium for microorganisms prepared according to the procedures used in Example 1, there was added 0.4 ml of sterilized water to thus make the medium wet. Then a dry face of a chopping board was directly stamped with the fiber layer side of the medium or directly wiped out with the fiber layer side of the medium, followed by addition of 0.6 ml of sterilized water to the culture medium, coverage thereof with a sterilized polypropylene film having a thickness of 0.04 mm and culture of microorganisms at 35° C. for 14 hours.

In every culture medium, there was observed the formation of red colonies which indicated the growth of the microorganisms.

Example 4

To one liter of water, there were added 50 g of polyvinyl alcohol having a degree of saponification of 88% and an average degree of polymerization of 1800 and 10 mg of 2,3,5-triphenyl tetrazolium chloride, followed by dissolution of these components, application of the resulting solution onto a polyester film having a thickness of 20 μm and a size of 1×1 m and then drying to form a polymeric compound layer B. Then there was applied, onto the layer B, a solution prepared by dissolving, in 500 ml of water, 20 g of a polyvinyl alcohol having a degree of saponification of 88% and an average degree of polymerization of 1800, followed by drying the coated solution to form a polymeric compound layer A. After semi-drying the layer A, a nonwoven fabric of rayon having a basis weight of 80 g/m², an average fiber diameter of 5 μm and a thickness of 1.2 mm was put on the layer A and then the resulting assembly was dried to form a material for culture media of the present invention. The material for culture media was cut into circular pieces each having a diameter of 50 mm. After adhering a polyester film having a thickness of 100 μm and a size of 70×80 mm to the circular medium from the polyester film side thereof, the culture medium was sterilized by the ethylene oxide gas sterilization.

The wet face of a chopping board washed with water was directly stamped with the material for culture media from its fiber layer side or directly wiped out with the material. Thereafter, 0.5 to 0.7 ml of an aqueous solution comprising, per one liter of water, 5 g of meat extract, 15 g of peptone, 5 g of sodium chloride and 5 g of potassium monohydrogen phosphate was added to the material, followed by coverage with a sterilized polypropylene film having a thickness of 0.04 mm and culture at 35° C. for 24 hours.

In addition, to the material for culture media, there was added 0.4 ml of sterilized water to thus make the medium wet. Then a dry face of a chopping board was directly stamped with the fiber layer side of the material or directly wiped out with the fiber layer side of the material, followed by addition of 0.6 ml of an aqueous solution comprising, per one liter of water, 5 g of meat extract, 15 g of peptone, 5 g of sodium chloride and 5 g of potassium monohydrogen phosphate to the material, coverage thereof with a sterilized polypropylene film having a thickness of 0.04 mm and culture of microorganisms at 35° C. for 14 hours.

In every culture medium, there was observed the formation of red colonies which indicated the growth of the microorganisms.

INDUSTRIAL APPLICABILITY

If using the culture medium of the present invention, it is easy to carry out the microbial tests of foods and environments. Moreover, the culture medium of the invention is also applicable to the microbial test of lanes having a curvature or unevenness to some extent by directly stamping or swabbing the subject to be inspected with the medium, in addition to the usual foods and environment test. The medium further permits the elimination of any contact between a color former or selecting agent, which may inhibit the growth of microorganisms, and the microorganisms at the initial stage of the culture thereof and therefore, the number of microorganisms grown on the medium can precisely be determined, since the medium is not accompanied by any reduction of the total viable count unlike the usual methods even if a color former or the like is incorporated into the medium. In case of the culture medium to which a selecting agent is added, the cell division of microorganisms is accelerated if any contact between the selecting agent and the microorganisms is inhibited at the earliest stage of the culture. Thus, they can be recognized with the naked eyes within a short period of time. The material for culture media and the culture medium according to the present invention are very small in thickness. Therefore, they can save space for culture of microorganisms and the amount of waste generated after the use thereof is greatly reduced as compared with the usual culture medium for microbial test. As has been described above, the material and culture medium of the present invention can be applied to a wide variety of subjects to be tested and make the microbial test quite easy.

What is claimed is:

1. A material for culture media comprising a fiber layer; a polymeric compound layer A free of a color former and a selecting agent; and a polymeric compound layer B containing a color former and/or a selecting agent, which are laminated together in this order, wherein the polymeric compound for the layers A and B is one whose 4% by weight aqueous solution has a viscosity, as determined at 20° C. of not less than 10 cps and the polymeric compound for at least one of the layers A and B is polyvinyl alcohol.

2. The material for culture media of claim 1 wherein the fiber layer comprises nylon fibers.

3. The material for culture media of claim 1 wherein the polymeric compound for the layers A and B is polyvinyl alcohol.

4. The material for culture media according to claim 1 further comprising nutrients required for the growth of microorganisms which nutrients are incorporated into at least one of the layers A and B and the fiber layer.

5. A material for culture media comprising a fiber layer; a polymeric compound layer A free of a color former and a selecting agent; and a polymeric compound layer B containing a color former and/or a selecting agent, which are laminated together in this order, wherein the polymeric compound for the layers A and B is polyvinyl alcohol, wherein the polyvinyl alcohol is one having a degree of saponification ranging from 75 to 90% and a molecular weight ranging from 30,000 to 200,000.

6. The material for culture media according to claim 5, wherein the fiber layer comprises nylon fibers.

7. The material for culture media according to claim 6 further comprising nutrients required for the growth of microorganisms which nutrients are incorporated into at least one of the layers A and B and the fiber layer.

8. The material for culture media according to claim 5 further comprising nutrients required for the growth of microorganisms which nutrients are incorporated into at least one of the layers A and B and the fiber layer.

9. A material for culture media comprising a fiber layer; a polymeric compound layer A free of a color former and a selecting agent; and a polymeric compound layer B containing a color former and/or a selecting agent, which are laminated together in this order, wherein the polymeric compound for the layers A and B is polyvinyl alcohol and wherein the polymeric compound for the layer A and B is one whose 4% by weight aqueous solution has a viscosity, as determined at 20° C., of not less than 10 cps, and wherein the polyvinyl alcohol is one having a degree of saponification ranging from 75 to 90% and a molecular weight ranging from 30,000 to 200,000.

10. The material for culture media according to claim 9, wherein the fiber layer comprises nylon fibers.

11. The material for culture media according to claim 10 further comprising nutrients required for the growth of microorganisms which nutrients are incorporated into at least one of the layers A and B and the fiber layer.

12. The material for culture media according to claim 9 further comprising nutrients required for the growth of microorganisms which nutrients are incorporated into at least one of the layers A and B and the fiber layer.

* * * * *